United States Patent [19]

Coker et al.

[11] 3,956,066

[45] May 11, 1976

[54] GLUCOSE ISOMERIZING ENZYME

[75] Inventors: Lowell E. Coker, Crete; Donald E. Gardner, Hazel Crest, both of Ill.

[73] Assignee: A. E. Staley Manufacturing Company, Decatur, Ill.

[22] Filed: Aug. 16, 1973

[21] Appl. No.: 389,054

[52] U.S. Cl. .................................. 195/31 F; 195/65
[51] Int. Cl.[2] .................. C12D 13/10; C12D 13/02
[58] Field of Search .................. 195/31 F, 66 R, 65, 195/62

[56] References Cited
UNITED STATES PATENTS

| | | | |
|---|---|---|---|
| 3,708,397 | 1/1973 | Sipos | 195/31 F |
| 3,753,858 | 8/1973 | Takasaki et al. | 195/31 F |
| 3,826,714 | 7/1974 | Suekane et al. | 195/31 F |

OTHER PUBLICATIONS

Ichimura et al., *Journal of Agricultural Chemical Society of Japan,* Vol. 39, pp. 291–298, (1965).
Takasaki et al., "Studies on Sugar-Isomerizing Enzyme", *Agr. Biol. Chem.,* Vol. 33, No. 11, pp. 1527–1534, (1969).
Strandberg et al., *Applied Microbiology,* Vol. 21, No. 4, pp. 588–593, (1971).

*Primary Examiner*—A. Louis Monacell
*Assistant Examiner*—Thomas G. Wiseman
*Attorney, Agent, or Firm*—M. Paul Hendrickson; Charles J. Meyersan

[57] ABSTRACT

There is provided an enzymatic process for interconverting aqueous solutions of dextrose and fructose with newly discovered glucose isomerases. The glucose isomerases are obtained from cultures of *Flavobacterium devorans* NRRL B-5384, *Flavorbacterium devorans* ATCC 10829, *Brevibacterium incertum* NRRL B-5383 and *Streptomyces phaeochromogenes* ATCC 15486.

35 Claims, No Drawings

GLUCOSE ISOMERIZING ENZYME

This invention relates to a process of enzymatically interconverting aqueous solutions of fructose and/or dextrose. More particularly, the invention relates to the enzymatic interconversion of fructose and dextrose with newly discovered glucose isomerases.

BACKGROUND OF THE INVENTION

Although starch-derived syrups and sugars, notably corn starch-derived dextrose and maltose syrups, are used on a large scale in the food industry, they fail to possess the sweetness of sucrose. The lack of sweetness limits their utility in the food industry. Fructose, the keto isomer of dextrose, is sweeter than dextrose, maltose and sucrose. Mixtures of dextrose and fructose are frequently comparable in sweetness to sucrose.

In the presence of a suitable catalyst, dextrose will convert to an isomeric ketose or keto sugar such as fructose. This catalytic reaction proceeds towards an equilibrium of the two sugars. Depending upon the isomerization conditions, the equilibrium is usually between about 45–55 parts fructose to about 55–45 parts dextrose. Solutions rich in either dextrose or fructose tend to assume the same equilibrium.

Heretofore, alkaline substances such as sodium hydroxide (e.g., see U.S. Pat. No. 2,354,664) and basic ion exchange resins (e.g., see U.S. Pat. No. 2,746,889) have been used in isomerization processes. Unfortunately, the alkaline isomerization processes develop undesirable by-products such as psicose, saccharic acid, inorganic residues, and color bodies (cf. U.S. Pat. No. 3,285,776). The formation of organic by-products reduces fructose yields and requires additional processing for their removal (e.g., see U.S. Pat. No. 3,383,245).

U.S. Pat. No. 2,950,228 by Marshall et al. discloses glucose isomerases useful in converting dextrose to fructose. Within recent years, a host of other glucose isomerases from divergent microbial sources have been proposed. Although the isomerases are more suitably adapted to isomerization processes, the use of isomerase preparations is not entirely free from disadvantages. It has been experienced that many of the isomerase preparations (e.g., Marshall, supra) are highly susceptible to inactivation at elevated temperatures. As a result, relatively low isomerization temperatures (e.g., well below 55°C.) over a more prolonged period of time are generally required to complete the isomerization process. When relatively low isomerization temperatures are employed, microbial infestations and by-products become a problem. Attempts to increase the isomerase activity rate by employing elevated temperatures are generally frustrated by the requirement of excessive and uneconomical amounts of isomerase. Many isomerase preparations suggested heretofore require the presence of objectionable or poisonous cofactors (e.g., arsenates) to effectively conduct the isomerization process. An isomerase preparation capable of isomerizating dextrose to fructose at relatively high temperatures without requiring the presence of objectionable cofactors would be beneficial in correcting the aforementioned disadvantages.

OBJECTS

It is an object of this invention to provide a process of isomerizing dextrose and fructose with glucose isomerases at elevated temperatures.

Another object is to improve reaction efficiency under conditions which inhibit microbial infestation.

A further object of this invention is to provide a process employing new sources of glucose isomerase possessing enhanced heatstability.

A still further objective is to provide glucose isomerases which are capable of interconverting dextrose to high fructose yields.

An additional object of the invention is to provide heat-stable isomerase preparations and a process for preparing the same.

ISOMERIZATION PROCESS

According to the present invention, there is provided a process for isomerizing hexoses, said process comprising the steps of:

a. providing an aqueous solution containing at least one hexose selected from the group consisting of dextrose and fructose;

b. subjecting the aqueous solution to a glucose isomerase preparation obtained from at least one microorganism selected from the group of *Flavobacterium devorans* NRRL B-5384, *Flavobacterium devorans* ATCC 10829, *Brevibacterium incertum* NRRL B-5383; and *Streptomyces phaeochromogenes* ATCC 15486; and c. maintaining the aqueous solution under isomerizing conditions sufficient to provide an aqueous solution containing the isomerized hexose.

As recognized by the art, any aqueous solution containing an appreciable amount of dextrose or fructose can be adapted to an isomerization process. The fructose yield in the isomerization process depends to a large extent upon the amount of dextrose initially present in the aqueous solution. The isomerization is generally unaffected by the presence of other sugars such as maltose, maltotriose, and higher glucose oligosaccharides. Accordingly, dextrose containing aqueous solutions ranging from malto dextrins to dextrose syrups or pure dextrose may be utilized. Corn starch syrups containing dextrose as a principal fermentable saccharide (e.g., syrups having a F.E. value of 45 or higher) are most suitably adapted for use as an aqueous solution. Higher fructose yields, on a dry substance basis, are obtained by employing a starch conversion syrup containing 90 percent by weight dextrose (on a dry solids basis) and preferably greater than about 95% by weight dextrose. Fragmatically, the dry substance of the aqueous solution will usually range from about 30% to about 60% by weight dry substance and preferably within about 45% by weight to about 55% by weight dextrose.

Pursuant to the present invention, the isomerization process is conducted by subjecting the glucose-containing solution to a glucose isomerase preparation obtained by cultivating at least one organism selected from the group consisting of *Flavobacterium devorans* NRRL B-5384, *Flavobacterium devorans* ATCC 10829, *Brevibacterium incertum* NRRL B-5383 and *Streptomyces phaeochromogenes* ATCC 15486. The isomerization with the isomerase preparation may be conducted on a batch or continuous basis. Deactivated cells containing the isomerase in the cell-bound form or a soluble isomerase preparation or isomerase dispersed in a suitable carrier, as well as mixtures thereof, are applicable. The glucose isomerase preparation may be directly admixed to the aqueous solution for the isomerization of dextrose to fructose. Upon completion of a batch-type isomerization process, active, cell-bound isomerase may be recovered (e.g., filtration or centrifugation) and recycled for further use. Similarly, dissolved glucose isomerase and released cell-bound glucose isomerase may be insolubilized by conventional means (e.g., insoluble carriers, by means of adsorption, entrapment, or covalent bonding) and recycled for reuse in either a continuous or batch type operation. For continuous isomerization processes, the isomerase preparation can be placed in a fixed bed or bed series with isomerizing of glucose-containing solution being accomplished by continuously passing the solution through the bed (e.g., see U.S. Pat. No. 3,694,314 by N. E. Lloyd et al.).

The isomerases herein disclosed are heat-stable and possess significantly enhanced isomerization activity when the interconversion is conducted at a relatively high temperature (e.g., at 55°C. or higher). Although excessively high temperatures will accelerate enzyme deactivation, isomerizing at temperatures of about 100°C. for a relatively short period of time (e.g., an hour) without experiencing total deactivation may be used. The isomerases exhibit significantly improved isomerization yields and activity rate at temperatures within the range of greater than about 65°C. to about 85°C. The isomerization process may be conducted, if desired, in the presence of other carbohydrases. Although not necessary, lower isomerization temperatures for a longer time interval may be employed.

The isomerization of dextrose to fructose herein is most suitably conducted at a pH between about 6.0 and 8.0. Under alkaline pH conditions, particularly above pH 8, adverse color formation and other detrimental side reactions become more prevalent. Isomerase activity is significantly reduced at pH's below 6.0. Significantly improved results are typically achieved when the isomerization is conducted at a pH between about 6.5–7.5 (preferably at about 7.0 ± 0.2).

Polyvalent cationic thermal stabilizing agents in an amount sufficient to inhibit thermal deactivation of the isomerase at elevated temperatures may be employed to improve the efficacy of the isomerization. Illustrative heat-stabilizing polyvalent cations such as cobalt, magnesium and manganese ions may be used to enhance the heat-stability of the glucose isomerase in the isomerization process in conjunction with heat-stabilizing anions such as chloride, sulfate, acetate, etc. The amount of heat-stabilizing polyvalent cations can be readily determined by comparing the temperature optimum of glucose isomerase preparations containing diverse amounts of the polyvalent cation.

Fructose concentrations of greater than 20 percent by weight (fructose-dextrose ratio 1:4 and higher) and preferably more than 35% are easily obtained by subjecting glucose-containing solutions to the isomerase preparations of the present invention. Since the rate of conversion of dextrose to fructose diminishes as the equilibrium point of the two hexoses is approached, the isomerization process is usually terminated when about 40 to about 50 percent by weight fructose (based upon total fructose and dextrose weight) is achieved.

As understood by the art, the isomerase units employed in the isomerization process can vary considerably. Period of treatment, degree of isomerization, temperature, etc. are factors which have a bearing upon the most suitable units for a particular process. Accordingly, the isomerization process can be accelerated by increasing the isomerase units and temperature. Conversely, lesser isomerase units and a lower isomerization temperature can be used to provide a comparable fructose yield at the expense of conducting the isomerization for a longer period of time. Although it is conceivable under certain circumstances to employ a very small amount of isomerase (e.g., one unit of isomerase activity as determined in accordance with the assay of Example 1 for each gram of dextrose on a d.s.b.), isomerization processes will usually require greater than about 5 units of isomerase activity per gram of dextrose solids (preferably more than about 10 units of isomerase preparation). For most commercial applications, about 15 units to less than about 25 isomerase units (preferably about 15–20 units) are employed. Since isomerase requirements are a major cost factor, the isomerization process is most suitably conducted under conditions which optimize the total isomerase activity of the isomerase preparation. Excessive amounts (e.g., greater than 40 units) become quite costly. Reference is made to U.S. Pat. No. 3,694,314 for illustrative fixed bed isomerase preparation requirements.

ISOMERASE PREPARATION

Pursuant to the present invention, there is also provided a process for producing novel glucose isomerase preparations by cultivation of an organism selected from the group consisting of *Flavobacterium devorans* NRRL B-5384, *Flavobacterium devorans* ATCC 10829, *Brevibacterium incertum* NRRL B-5383 and *Streptomyces phaeochromogenes* ATCC 15486 under conditions and for a length of time sufficient to produce at least 15 units of glucose isomerase activity) as determined per the assay of Example 1) and having an isomerase preparation temperature optimum of at least about 65°C. as determined by the amount of fructose produced from dextrose in one hour. These organisms produce cell-bound or intracellular, as well as soluble or extracellular glucose isomerase, with both forms being applicable to the isomerization process.

The newly isolated organisms Brevibacterium and Flavobacteriaceae were identified in accordance with Bergey's Manual of Determinative Bacteriology, 7th edition, Baltimore, 1957 as follows:

*Brevibacterium incertum* NRRL B-5383

Short stubby rods; no spores seen
Growth on nutrient agar slants: scarce; colorless to yellow colony
Nitrate reduction: negative
Potato slant: white to grayish growth

*Flavobacterium devorans* NRRL B-5384

Morphology: Medium long, narrow rods appearing singly and paired
Growth on nutrient agar: scarce; yellow colony
Nitrate reduction: negative
Potato slant: very slow growth Although diverse mediums may be used in cultivating the four organisms, the organisms are most suitably cultivated on a nutrient medium containing carbohydrate, nitrogen, xylose and nutritive salts. With the aid of other carbon sources, the glucose isomerases can be obtained by cultivating these organisms in the absence of xylose. Increased isomerase yields are obtained in the presence of xylose with xylose in the culture medium at about 0.4–1.5 percent concentration being preferred. Higher xylose concentrations which do not interfere with glucose isomerase production may be employed. Carbohydrate sources of carbon which may be partially substituted for xylose include ground yellow dent corn, ground white corn, potatoes, starch, sucrose, corn syrup, ground oats, barley, wheat, beet pulp, organic pulp and the like. The nitrogen source can be in the organic or inorganic form and may be, for example, urea, ammonium salts such as ammonium chloride, ammonium phosphate, and ammonium sulfate, peptone, corn steep liquor, wheat bran extracts, cottonseed meal, autolyzed brewer's yeast and the like.

Unless the organisms are cultivated in the presence of certain nutrients and culturing conditions which induce the organisms to produce isomerase, the culture mediums fail to produce a sufficient amount of isomerase to be useful in an isomerization process. The presence of magnesium and manganous ions in the media have been found to be particularly effective in inducing the culture to produce the isomerase. Cobalt ion has also been found to be an important factor in obtaining an appropriate isomerase activity.

Cell growth and isomerase yields are significantly improved by conducting the cultivation under aerobic conditions. Uniform distribution of an effective amount of oxygen throughout the culture medium significantly enhances isomerase production. Turbulent conditions, such as mechanical agitation, may be utilized to effectuate uniform distribution of the aerating gas in the culture medium provided the shearing forces are not excessive (e.g., excessive mechanical shearing which inhibits or destroys cell growth). The higher glucose isomerase yields are generally characterized as being predominantly intracellular isomerase with a minor amount of extracellular enzyme. Aerating conditions which provide an isomerase preparation having a cell bound to extracellular glucose isomerase activity of at least 1:1 are particularly conducive to high isomerase yields.

Cell cultivation under controlled aerating conditions significantly enhance the isomerase yield. The effect of aerating conditions upon isomerase yields is illustrated by the cultivation of the isomerase producing organisms in a 14-liter capacity New Brunswick MF 114 Fermentator. Fermentations (e.g., at 11–13 liter fermentation broth) with air supply in the range of 0.1–1.0 v.v.m. (volume air per volume broth per minute) and a stirrer speed at 100–700 r.p.m. being generally conducive to improved enzyme yields. Further improvements are achieved when the aeration is at 0.45–0.85 v.v.m. at a 300–500 r.p.m. stirrer speed. Optimum isomerase yields are achieved when the aeration is carefully maintained between 0.65–0.75 v.v.m. and the stirrer speed at about 400 ± 25 r.p.m. Oxygen starvation (e.g., insufficient aeration) results in a lower total yield of isomerase activity and a higher proportion of soluble activity probably owing to the dying-off and lysing of cells. Fermentation for about 1 to 2 days at a pH of 6.7 will generally produce satisfactory yields. Upon completion of the fermentation, the cell-bound isomerase is conveniently recovered by filtration or centrifugation and washing. The cell-bound isomerase may be released by conventional means such as sonication, trituration, or autolysis.

The isomerase preparations prepared in accordance with the present invention possess a significantly higher isomerase activity comparative to the indigenous organisms which have not been induced to produce isomerase. Isomerase preparations isolated herein generally possess greater than 750 units of isomerase activity per gram of dry substance solids (e.g., deactivated, washed cells + isomerase) with most isomerase preparations being generally characterized as having an isomerase activity in excess of 2,500 units per gram of dry substance of deactivated cells. Isomerase preparations containing inactivated organisms possessing greater than 4,500 units of isomerase activity (preferably greater than about 5,000 such as illustrated in Table 1 of Example 1) may easily be obtained from the organisms *Brevibacterium incertum* NRRL B-5383, *Flavobacterium devorans* ATCC 10829 and *Streptomyces phaeochromogenes* ATCC 15486 by cultivation under the conditions herein to induce isomerase production. As well understood by the art, further isolation of the isomerase from inactivated cells to provide an isomerase preparation substantially free from other contaminants (e.g., an essentially pure isomerase preparation) will significantly increase the isomerase activity of the isomerase preparation on a dry substance basis.

The following examples are merely illustrated and should not be construed as limiting the scope of the invention.

EXAMPLE 1

*Flavobacterium devorans* NRRL B-5384, *Flavobacterium devorans* ATCC 10829, *Brevibacterium incertum* NRRL B-5383 and *Streptomyces phaeochromogenes* ATCC 15486 were each grown aerobically for 48 hours in the selective enrichment medium containing the following: 1.5% Trypticase (Baltimore Biological Laboratories), 0.5% neopeptone (Difco 0119-01), 0.5% sodium chloride, 0.1% dry yeast extract (Difco), 0.001% manganous sulfate monohydrate, 0.001M cobaltous chloride and 1.0% xylose. The resultant cultures were then washed with water and resuspended in water which had been adjusted to a cell concentration of 10 mg. of dry substance per ml.

Cellular activity (CA) was determined on washed cells and expressed as units/mg. cells/hr. (d.s.b.). Enzyme unit values were ascribed in terms of cellular isomerase preparation on a dry weight basis. Enzyme yields for the resultant isomerase preparations were calculated from the product of the cellular activity and cell yield. To determine enzyme yield values, three separate dry weight determinations were necessary. These determinations were made as follows:

Cell Yield

Two separate dry weight determinations are required to accurately express cell yield. Separate 2.0 ml. aliquots of whole culture beer and cell-free supernatant are added to tared aluminum weighing pans. The cell yield per ml. of whole culture beer is determined by subtracting the weight of non-cellular medium solids in the cell-free supernatant from that of the whole culture beer. The cell yield is then expressed as mg. cells per ml. whole culture beer.

Cellular Activity

One dry weight determination is necessary to express the amount of cells in the enzyme assay or cellular activity determination. One ml. of the washed cell suspension is added to a tared aluminum dish and dried as described below. The dry weight of cells in the assay aliquot may then be calculated.

Drying Conditions

The aqueous cell suspensions are dried in a convection oven for 70 minutes at 85°C. These conditions produce dried samples without any charring.

Assay for Units of Isomerase Activity

The assay for isomerase activity was carried out as follows:
The substrate solution consisted of 1 molar gulcose solution buffered at pH 7 with 0.2 molar potassium phosphate and containing 0.01 molar proportions of magnesium sulfate heptahydrate and 0.001 molar proportions of cobaltous chloride. To 4 ml. of the substrate solution, 0.5 or 1.0 ml. of the diluted cell suspension (i.e., 10 mg. dry substance/ml. $H_2O$) was added, followed by 0.5 ml. water when only 0.5 ml cell suspension was used.

After 60 minutes at 70°C., samples of the substrate solution were withdrawn, and subjected to ketose determination by a modified Seliwanoff test as follows:

A sample containing 0–60 mg. fructose was added to a 5.0 ml. volume of resorcinol reagent containing 0.050% resorcinol in 4N hydrochloric acid. The mixture of fructose solution and resorcinol reagent was heated for exactly 7 min. at 80°C., cooled for at least 5 min. at about 5°C. and within 15–30 min. after cooling, the percent transmittance of the sample was determined against a reagent blank at 440 millimicron wavelength, on a Spectronic 20 colorimeter.

One unit of isomerase activity was defined as being equivalent to the quantum of isomerase capable of producing one mg. of fructose in one hour in accordance with the aforementioned assay.

The qualitative Seliwanoff test for ketose sugars was published in Ber. 20, 181 (1887). The modified Seliwanoff test employed here is more convenient than the cysteine-carbazole test for ketoses as used in U.S. Pat. No. 2,950,228; results obtained by both methods have been found to be in satisfactory agreement.

The results of this example are set forth in Table 1.

TABLE 1

COMPARATIVE YIELDS OF GLUCOSE ISOMERIZING ENZYMES

| Organisms | CA[1] | Enzyme Yield[2] Cellbound/ml. | "Soluble"/ml. | Total/ml. |
|---|---|---|---|---|
| Brevibacterium incertum NRRL B-5383 | 4.91 | 23.65 | 8.88 | 32.53 |
| Flavobacterium devorans NRRL B-5384 | 5.63 | 20.1 | 10.25 | 30.35 |
| Flavobacterium devorans ATCC 10829 | 0.89 | 4.48 | 11.75 | 16.23 |
| Streptomyces phaeochromogenes ATCC 15486 | 4.93 | 17.18 | 6.87 | 24.05 |

[1]Cellular Activity (CA) determined on washed cells and expressed as units/mg. cells/hr. (d.s.b.)
[2]Cell bound enzyme yield = CA × mg. dry cells/ml. culture, expressed as units/ml. whole culture. "Soluble" enzyme yield = units/ml. of cell free supernatant. Total enzyme yield is the sum of cell bound and "soluble" enzyme and is expressed as units/ml. whole culture.

EXAMPLE 2

Example 1 was repeated in a 14-liter capacity New Brunswick MF Fermentator operated at one volume of air per minute for each volume of culture with mechanical stirring at 300 r.p.m. The results of this example are set forth in Table 2.

TABLE 2

Glucose Isomerase Activity Yield, Units/ml.

| Organism | Hours | Cell-Bound | Soluble | Total |
|---|---|---|---|---|
| Brevibacterium incertum NRRL B-5383 | 45 | 76 | 15 | 93 |
| Flavobacterium devorans NRRL B-5384 | 26 | 6 | 10 | 16 |
| Streptomyces phaeochromogenes ATCC 15486 | 28 | 126 | 10 | 136 |

In this example, the amount of cell-bound enzyme yields can be increased by increasing the nitrogen nutrient level.

EXAMPLE 3

The optimum isomerase activity temperature for Brevibacterium incertum NRRL B-5383, Flavobacterium devorans NRRL B-5384 and Streptomyces phaeochromogenes ATCC 15486 was determined in accordance with the substrate and methodology of Example 1. The amount of dextrose (mg.) produced in one hour at the designated temperature is set forth in Table 3.

TABLE 3

| Organism | Temperature, °C. | | | | |
|---|---|---|---|---|---|
| | 65 | 70 | 75 | 80 | 85 |
| Flavobacterium devorans NRRL B-5384 | .17 | .52 | 1.70 | 1.76 | 2.86 |
| Brevibacterium incertum NRRL B-5383 | 2.34 | 3.65 | 3.95 | 4.84 | 3.60 |
| Streptomyces phaeochromogenes ATCC 15486 | 3.24 | 5.53 | 5.52 | 7.0 | 6.94 |

A blank run consisting of a similar incubation omitting the addition of enzyme showed that no significant amount of non-enzymatic isomerization occurred.

As illustrated in Table 3, the optimum isomerization temperature for the NRRL B-5384 culture was greater than 80°C. with culture NRRL B-5383 and ATCC 15486 exhibiting an optimum temperature at about 80°C.

EXAMPLE 4

A dextrose substrate solution was prepared from 4,360 g. dextrose, 1.48 g. cobaltous chloride hexahydrate, 15.32 g. magnesium sulfate heptahydrate and 2,840 ml. distilled water; the solution was adjusted to pH 6.9 with 0.375 normal sodium hydroxide and further diluted to 54.00% solids. It was subjected to the action of 5 units glucose isomerase Brevibacterium incertum NRRL B-5384/g. dextrose for 18 hr. at 70°C. Initial fructose production measured by polarimetry was 1,155 mg./hr. as against a predicted production (for 5 units glucose isomerase/g. dextrose input) of 1,145 mg./hr.

EXAMPLE 5

This example illustrates the conversion of dextrose to fructose by the action of cellular *Flavobacterium devorans* NRRL B-5384 enzyme and cellular *Brevibacterium incertum* NRRL B-5383 enzyme on a dextrose solution at about pH 6.9 at 70°C., with different isomerase activity input and reaction times.

The dextrose solutions employed in this example were made up as follows: 4,360 g. dextrose (95.6% dry substance basis) was mixed with 2,840 ml. water and warmed to solution; about 4 g. sodium bisulfite, 1.5 g. cobaltous chloride hexahydrate and 15.3 g. magnesium sulfate heptahydrate was added, the medium adjusted to pH 6.9 with 0.375 N sodium hydroxide, and water was added to establish a refractive index about 1.4242 to 1.4252. To 500 ml. portions of the thus prepared medium, the stated volumes of enzyme cell solution was added and the dextrose-enzyme mixture incubated at 70°C.; the pH was adjusted to 6.9 as needed by means of 0.375 N sodium hydroxide.

In Tables 4 and 5, the results of this example are tabulated.

TABLE 4

ISOMERIZATION BY WHOLE CULTURE[1]
FLAVOBACTERIUM DEVORANS NRRL B-5384

| Enzyme Units/ | ml. Cell | % Fructose[2] | |
| Gram Dextrose | Suspension | 24 Hrs. | 46 Hrs. |
| --- | --- | --- | --- |
| — | — | — | — |
| 36 | 250 | 32.8 | 43.3 |
| 72 | 500 | 39.4 | 44.6 |

[1]The whole culture medium assayed at 40 units/ml./hr.
[2]Percent fructose by polarimetry.

TABLE 5

ISOMERIZATION BY CELLULAR
BREVIBACTERIUM INCERTUM NRRL B-5383

| Enzyme units/gram dextrose | % Fructose[1] | |
| ml. cell suspension | 24 hrs. | 48 hrs. |
| --- | --- | --- |
| 40 | 21.2 | 33.1 |
| 80 | 32.0 | 46.2 |
| 120 | 42.5 | 49.8 |

[1]Percent fructose by gas-liquid chromatography.

Since many embodiments may be made of this invention and since many changes may be made in the embodiments described, the foregoing description is to be considered as illustrative only and the invention is defined in the appended claims.

What is claimed is:

1. A process for isomerizing hexose with a heat-stable isomerase suitable for use in a dextrose isomerization process conducted at a temperature of 70°C. for a period of time sufficient to provide an isomerized aqueous solution which contains on a dry solids weight basis a fructose to dextrose weight ratio of at least about 1 to 4, said process comprising the steps of:
   a. providing an aqueous solution containing at least one hexose selected from the group consisting of dextrose and fructose;
   b. subjecting the aqueous solution to a glucose isomerase obtained from a microorganism selected from the group of *Flavobacterium devorans* NRRL B-5384, *Flavobacterium devorans* ATCC 10829, *Brevibacterium incertum* NRRL B-5383; and *Streptomyces phaeochromogenes* ATCC 15486; and
   c. maintaining the aqueous solution under isomerizing conditions sufficient to provide an isomerized hexose.

2. The process according to claim 1 wherein the aqueous solution is a starch hydrolyzate comprising dextrose as the principal fermentable saccharide on a dry solids basis.

3. The process according to claim 2 wherein the isomerization is conducted at a temperature of at least 55°C.

4. The process of claim 3 wherein the isomerization is conducted at a pH of between about 6.0 to about 8.0 and a temperature greater than about 65°C.

5. The process according to claim 3 wherein the isomerization is conducted at a pH of between 6.8 and 7.2.

6. The process according to claim 4 wherein the isomerization is conducted in the presence of a polyvalent cationic thermal stabilizing agent in an amount sufficient to enhance isomerase activity by heat stabilization of the glucose isomerase at the temperature employed in the isomerization of the hexose.

7. The process according to claim 1 wherein the aqueous solution contains a starch hydrolyzate consisting of at least 90 percent dextrose on a dry solids weight basis.

8. The process according to claim 7 wherein the isomerization step is conducted for a period of time and under conditions sufficient to provide an isomerized aqueous solution containing a fructose to dextrose ratio of at least 1:4 and a temperature of greater than about 70°C. is used during the isomerization thereof.

9. The process according to claim 7 wherein the isomerization of dextrose to fructose is conducted at a pH of between about 6.0 to about 8.0 in the presence of at least one polyvalent cationic thermal stabilizing agent selected from the group consisting of cobalt, manganese and magnesium ions with the amount of thermally stabilized agent being sufficient to enhance the activity by heat stabilization of the glucose isomerase at the temperature the isomerization is conducted.

10. The process according to claim 9 wherein the glucose isomerase consists essentially of a *Brevibacterium incertum* NRRL B-5383 glucose isomerase.

11. The process according to claim 9 wherein the glucose isomerase consists essentially of a *Flavobacterium devorans* NRRL B-5384 glucose isomerase.

12. The process according to claim 9 wherein the glucose isomerase consists essentially of a *Flavobacterium devorans* ATCC 10829 glucose isomerase.

13. The process according to claim 9 wherein the glucose isomerase consists essentially of a *Streptomyces phaeochromogenes* ATCC 15486 glucose isomerase.

14. The process according to claim 10 wherein the isomerization step is conducted in the presence of an effective amount of the glucose isomerase to isomerize the dextrose to fructose and at a temperature between about 65° to about 85°C. for a period of time sufficient to provide an isomerized aqueous solution which contains on a dry solids weight basis a fructose to dextrose ratio of at least about 1 to 4.

15. The process according to claim 11 wherein the isomerization step is conducted in the presence of an effective amount of the glucose isomerase and at a temperature between about 65° to about 85°C. for a period of time sufficient to provide an isomerized aqueous solution which contains on a dry solids weight basis a fructose to dextrose ratio of at least about 1 to 4.

16. The process according to claim 12 wherein the isomerization step is conducted in the presence of an effective amount of the glucose isomerase and at a temperature between about 65° to about 85°C. for a period of time sufficient to provide an isomerized aqueous solution which contains on a dry solids weight basis a fructose to dextrose ratio of at least about 1 to 4.

17. The process according to claim 13 wherein the isomerization step is conducted in the presence of an effective amount of the glucose isomerase and at a temperature between about 55° to about 80°C. for a period of time sufficient to provide an isomerized aqueous solution which contains on a dry solids weight basis a fructose to dextrose ratio of at least about 1 to 4.

18. A process of producing glucose isomerase by cultivating an organism selected from the group consisting of *Flavobacterium devorans* NRRL B-5384, *Flavobacterium devorans* ATCC 10829, *Brevibacterium incertum* NRRL B-5383; and *Streptomyces phaeochromogenes* ATCC 15486 under conditions and for a length of time sufficient to produce at least 15 units glucose isomerase having a temperature optimum of at least about 65°C. as determined by the amount of fructose produced from dextrose in 1 hour.

19. A process according to claim 18 wherein the organism is *Brevibacterium incertum* NRRL B-5383 glucose isomerase.

20. A process according to claim 18 wherein the organism is *Flavobacterium devorans* NRRL B-5384 glucose isomerase.

21. A process according to claim 18 wherein the organism is *Flavobacterium devorans* ATCC 10829 glucose isomerase.

22. A process according to claim 18 wherein the organism is *Streptomyces phaeochromogenes* ATCC 15486 glucose isomerase.

23. The process according to claim 19 wherein the cell cultivation is conducted under aerobic aerating conditions sufficient to provide an isomerase having a ratio of cell-bound to extracellular glucose isomerase activity of at least 1 to 1.

24. The process according to claim 20 wherein the cell cultivation is conducted under aerobic aerating conditions sufficient to provide an isomerase having a ratio of cell-bound to extracellular glucose isomerase activity of at least 1 to 1.

25. The process according to claim 22 wherein the cell cultivation is conducted under aerobic aerating conditions sufficient to provide an isomerase having a ratio of cell-bound to extracellular glucose isomerase activity of at least 1 to 1.

26. The process according to claim 18 wherein the cell cultivation is conducted in the presence of an effective amount of cobalt ion sufficient to enhance isomerase activity.

27. A heat-stable, isomerase suitable for use in a dextrose isomerization process conducted at temperatures of at least 70°C. for a period of time sufficient to provide an isomerized aqueous solution which contains on a dry solids weight basis a fructose to dextrose weight ratio of at least about 1:4 said isomerase characterized as possessing an isomerase activity of greater than 750 units per gram of dry substance, an optimum isomerase activity temperature of greater than 65°C., and the isomerase is derived from at least one organism selected from the group consisting of *Flavobacterium devorans* NRRL B-5384, *Flavobacterium devorans* ATCC 10829, *Brevibacterium incertum* NRRL B-5383, and *Streptomyces phaeochromogenes* ATCC 15486.

28. The isomerase according to claim 27 wherein the isomerase activity is greater than 2,500 units per gram of dry substance and the optimum isomerization temperature for the isomerase is greater than about 75°C.

29. The isomerase preparation according to claim 28 wherein the organism is *Brevibacterium incertum* NRRL B-5383 glucose isomerase.

30. The isomerase according to claim 29 wherein the isomerase activity is greater than 4,500 units per gram of dry substance.

31. The isomerase according to claim 28 wherein the organism is *Flavobacterium devorans* NRRL B-5384 glucose isomerase.

32. The isomerase according to claim 31 wherein the isomerase activity is greater than 2,500 units per gram of dry substance and the optimum isomerization temperature for the isomerase is greater than about 75°C.

33. The isomerase according to claim 28 wherein the organism is *Streptomyces phaeochromogenes* ATCC 15486 glucose isomerase.

34. The isomerase according to claim 33 wherein the isomerase activity is greater than 4,500 units per gram of dry substance.

35. The isomerase according to claim 27 wherein the organism is *Flavobacterium devorans* ATCC 10829 glucose isomerase.

\* \* \* \* \*

UNITED STATES PATENT AND TRADEMARK OFFICE
CERTIFICATE OF CORRECTION

PATENT NO. : 3,956,066
DATED : May 11, 1976
INVENTOR(S) : Lowell E. Coker and Donald E. Gardner It is certified that error appears in the above-identified patent and that said Letters Patent are hereby corrected as shown below:

Column 1, line 65, for "isomerizating" read ---isomerizing---
Column 2, line 10, for "heatstability" read ---heat-stability---
Column 2, line 53, for "Fragmatically" read ---Pragmatically---
Column 7, line 13, for "gulcose" read ---glucose---
Column 12, line 26, for "isomerase preparation according" read ---isomerase according---

Signed and Sealed this

Twenty-ninth Day of March 1977

[SEAL]

Attest:

RUTH C. MASON
Attesting Officer

C. MARSHALL DANN
Commissioner of Patents and Trademarks